(12) United States Patent
Cernik et al.

(10) Patent No.: US 7,253,317 B2
(45) Date of Patent: Aug. 7, 2007

(54) METHOD FOR FLUORINATING A COMPOUND COMPRISING A HALOSULPHONYL OR DIHALOPHOSPHONYL GROUP

(75) Inventors: Milos Cernik, Brno (CZ); Antonin Ruzicka, Olomucany (CZ); Zdirad Zak, Brno (CZ); Virginie Pevere, Lyons (FR); Christophe Michot, Grenoble (FR)

(73) Assignee: Hydro-Quebec, Montreal (Quebec) (CA)

( * ) Notice: Subject to any disclaimer, the term of this patent is extended or adjusted under 35 U.S.C. 154(b) by 123 days.

(21) Appl. No.: 10/451,920

(22) PCT Filed: Dec. 21, 2001

(86) PCT No.: PCT/FR01/04164

§ 371 (c)(1),
(2), (4) Date: Dec. 3, 2003

(87) PCT Pub. No.: WO02/053494

PCT Pub. Date: Jul. 11, 2002

(65) Prior Publication Data

US 2004/0097757 A1 May 20, 2004

(30) Foreign Application Priority Data

Dec. 29, 2000 (FR) .................. 00 17307

(51) Int. Cl.
C07C 303/02 (2006.01)
C07C 303/08 (2006.01)
(52) U.S. Cl. .............. 564/95; 564/80; 568/30
(58) Field of Classification Search ........ 429/307; 546/2; 548/101; 556/18; 359/237; 526/100; 562/818, 825
See application file for complete search history.

(56) References Cited

OTHER PUBLICATIONS

Burkhard et al., Inorganic Chemistry (1998), 37(24), 6295-6303.*

Ruff et al., "Imidodisulfuryl fluoride, cesium imidodisulfuryl fluoride and fluoroimidodisulfuryl fluoride", Inorganic Synthesis, vol. 11, 1968, pp. 138-143, XP001027947.

Appel et al., "Die synthese des imidobisschwefelsaurefluorids, $HN(SO_2F)_2$", Chem. Ber., vol. 95, 1962, pp. 246-248, XP002179138.

Barbour, et al., "The preparation of organic fluorine compounds by halogen exchange", Advances in Fluorine Chemistry, XX, XX, vol. 3, 1963, pp. 181-250, XP001027931.

Sartori et al., "Elektrochemische Perfluorierung mit Mehrkomponenten-Elektrolyten", Dechema Monographien: Electrochemische Stoffgewinnung-Grundlagen und Verfahrenstechnik, vol. 125, 1992, pp. 233-242, XP001028663.

* cited by examiner

*Primary Examiner*—Karl Puttlitz
(74) *Attorney, Agent, or Firm*—Buchanan Ingersoll & Rooney

(57) ABSTRACT

The invention relates to a fluorination process for producing fluorinated compounds.

The process consists in reacting a compound (I) corresponding to the formula

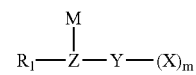

with an ionic fluoride of a monovalent cation. M represents H, an alkali metal, a quaternary phosphonium group or a quaternary ammonium group. Y represents $SO_2$ and m is 1, or else Y is PO and m is 2. Z represents $CR^2$, N or P. $R^1$ represents an electron-withdrawing group which has a Hammet $\sigma_P$ parameter of greater than 0.4. $R^2$ represents a carbonaceous and/or electron-withdrawing group. X represents a halogen other than a fluorine.

The fluorinated compounds obtained are of use in particular as electrolytes in lithium batteries.

23 Claims, No Drawings

METHOD FOR FLUORINATING A COMPOUND COMPRISING A HALOSULPHONYL OR DIHALOPHOSPHONYL GROUP

This application is filed under 35 USC 371, from PCT/FR01/04164, filed Dec. 21, 2001.

BACKGROUND OF THE INVENTION

1. Field of the Invention

The invention relates to a fluorination process for producing fluorinated compounds which can be used in particular as electrolyte.

2. Description of the Related Art

Lithium batteries, in which the anode is formed by a sheet of lithium metal or by a lithium alloy and which operate by movement of lithium ions between the electrodes, have been widely studied. However, their development has been impeded due to the fact that, during their recharging, deposition of lithium metal of dendritic nature occurs, which can lead to short-circuits, resulting in an explosion in the system. This risk has been eliminated by replacing the lithium or lithium alloy anode by an anode composed of a carbonaceous material in which the lithium ions can be reversibly inserted. This novel form of lithium batteries, known as "lithium-ion" batteries, is widely used in the field of portable electronic equipment. The electrolyte of these batteries comprises at least one lithium salt in solution in an organic solvent which can be a polar aprotic liquid solvent (for example, ethylene carbonate, propylene carbonate or a dialkyl carbonate) optionally supported by a porous plastic support, a polar polymer [for example, a crosslinked poly(ethylene oxide)] or a liquid solvent gelled by a polymer. The lithium salt plays an important role in the operation of the battery. The most widely used salt is $LiPF_6$, which makes it possible to obtain liquid electrolytes which have a conductivity of greater than $10^{-2}$ S.cm$^{-1}$ at ambient temperature. However, it has a limited thermal stability, which results in the formation of LiF and of HF, said HF leading to decomposition of the electrolyte which can result in an explosion in the battery. The lithium salt of bis(trifluoromethanesulfonyl)imide has been envisaged for replacing $LiPF_6$, but it exhibits the disadvantage of resulting in depassivation of the aluminum current collector of the cathode.

The use of imide salts or methane salts having $FSO_2$ or $F_2PO$ electron-withdrawing groups was then studied (WO 95/26056). These salts make it possible to obtain electrolytes with a greater conductivity than their homologues comprising perfluoroalkyl groups instead of the fluorine atoms and they result in markedly lower corrosion of the aluminum collectors. The use of an imide salt or methane salt comprising $FSO_2$ or $F_2PO$ groups thus makes it possible to maintain the low level of corrosion observed with $LiPF_6$ while improving the thermal stability with respect to that of $LiPF_6$.

Various processes for the preparation of imide salts or methane salts comprising at least one $FSO_2$ or $F_2PO$ group have been described. For example, bis(fluorosulfonyl)imide $(FSO_2)_2NH$ can be prepared by reaction of fluorosulfonic acid $FSO_3H$ with urea $H_2NC(O)NH_2$. The imide is subsequently isolated by treatment of the reaction mixture with NaCl in dichloromethane, followed by distillation of the pure acid [Appel & Eisenhauer, Chem. Ber., 95, 246–8, 1962]. However, the toxicity and the corrosive nature of $FSO_3H$ constitute a major disadvantage.

Another process consists in reacting $(ClSO_2)_2NH$ with $AsF_3$. The acid $(FSO_2)_2NH$ is subsequently isolated by treating the reaction mixture with NaCl in dichloromethane [Ruff and Lustig, Inorg. Synth., 1968, 11, 138–43]. The disadvantage of this process lies in particular in the high cost of $AsF_3$, in its toxicity and in the risk of contaminating the compound obtained.

For the phosphoryl derivatives, a process for the preparation of $LiN(POF_2)_2$ consists in reacting $LiN(SiMe_3)_2$ with $POF_3$. The removal of volatile $Me_3SiF$ results directly in the expected product [Fluck and Beuerle, Z. Anorg. Allg. Chem., 412(1), 65–70, 1975]. The disadvantage of this process lies in the cost of the silylated derivative and the use of gaseous and toxic $POF_3$.

It is known to prepare a fluorinated compound from the corresponding halogenated compound by a halogen exchange reaction using an ionic halide, such as, for example, KF or CsF, or an organic fluoride, such as tetra(n-butyl)ammonium fluoride. The reaction is a nucleophilic substitution which preferably takes place in a polar aprotic solvent. The exchange reaction is promoted by the presence of a phase transfer catalyst chosen, for example, from quaternary ammonium salts, crown ethers, pyridinium salts or quaternary phosphonium salts. This process has been carried out with KF in particular to obtain monofluoroalkanes, α-fluoroesters, fluoroethers, acyl fluorides or sulfonyl fluorides respectively from the corresponding monohaloalkanes, α-haloesters, haloethers, acyl halides or sulfonyl halides [A. Basbour et al. in M. Stacy and co-editors, Advances in Fluorine Chemistry, Vol. 3, Butterworth, Washington D.C., 1963, pp. 181–250].

SUMMARY OF THE INVENTION

The inventors have now found that, surprisingly, the halogen/fluorine exchange process can be employed for the fluorination of various compounds comprising at least one halosulfonyl or dihalophosphryl group attached to an atom carrying at least one strongly electron-withdrawing substituent and optionally an acidic hydrogen.

The aim of the present invention is consequently to provide a process for the fluorination of a compound comprising at least one halosulfonyl or dihalophosphoryl group in which the halogen is other than a fluorine and at least one strongly electron-withdrawing group, for the purpose in particular of the preparation of the corresponding compounds comprising at least one fluorosulfonyl or difluorophosphoryl group.

The fluorination process according to the present invention consists in reacting, optionally in a solvent, a fluorinating agent with a compound (I) comprising a halosulfonyl or dihalophosphoryl substituent in which the halogen is other than a fluorine, wherein the fluorinating agent is an ionic fluoride of a monovalent caton and wherein the compound (I) corresponds to the following formula:

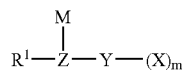

in which:

M represents H, an alkali metal, a quaternary phosphonium group or a quaternary ammonium group;

Z represents $CR^2$, N or P;

Y represents $SO_2$ and m is 1, or else Y is PO and m is 2;

$R^1$ represents an electron-withdrawing group which has a Hammett σp parameter of greater than 0.4;

$R^2$ represents a carbonaceous and/or electron-withdrawing group;

X represents a halogen other than a fluorine.

The process is particularly preferred for the compounds in which Z represents N.

DETAILED DESCRIPTION OF THE PREFERRED EMBODIMENTS

The process is advantageously carried out at atmospheric pressure, at a temperature of less than 180° C. The temperature is preferably less than 100° C., more particularly less than 80° C. An excessively slow reaction rate results from carrying out the process at a temperature below ambient temperature. The reaction medium can be heated by conventional means. Heating can also be carried out using microwaves. Stirring the reaction medium or applying ultrasound is of use in replacing the active surface of the reactants when they are in suspension.

The monovalent ionic fluoride can be an alkaline fluoride or a fluoride of a stable onium cation. Among alkali metals, it is advantageous to use K or Cs. Among onium cations, tetraalkylammonium, tetraalkylphosphonium or dialkylsulfonium cations are preferred. Onium cations in which the alkyl radicals (which can be identical or different in an onium cation) have from 1 to 12, more particularly from 1 to 4, carbon atoms are preferred. The abovementioned onium fluorides are advantageous because of their high solubility in organic solvents. They can therefore be used alone or in combination with a less soluble ionic fluoride, for which they then act as charge transfer catalyst. When the cation M of the compound (I) is al alkali metal or an onium as defined above for the fluoride, it is advantageous to use a fluoride of said cation M. The use of LiE or of NaF, although giving relatively slow reactions, is advantageous when the fluorinated product obtained from the compound (I) is intended to be used as electrolyte. It is preferable to use an ionic fluoride having a high active surface.

The amount of ionic fluoride used with respect to the amount of compound (I) is preferably greater than stoichiometry. The ratio of the number of moles of fluoride to the number of halogen atoms to be exchanged of the compound (I) is advantageously from 1.1 to 2. When the compound (I) is an imide [M is H in the formula (I)], said ratio is preferably greater than 2, more particularly greater than 3.

The process of the present invention is particularly suitable for the fluorination of compounds (I) in which M is H or an alkali metal, for example chosen from Na, K, Li or Cs. When M is a quaternary ammonium or a quaternary phosphonium, it corresponds respectively to the formulae $N(R^3R^4R^5R^6)$ and $P(R^3R^4R^5R^6)$ in which the various substituents $R^i$ are chosen, independently of one another, from alkyl radicals preferably having from 1 to 12, more particularly from 1 to 4, carbon atoms.

$R^1$ is an electron-withdrawing radical having a Hammett σp parameter of greater than 0.4. The radicals having a σp of greater than 0.5, more particularly of greater than 0.7, are particularly preferred. Preferably, the radical $R^1$ does not carry a positive charge at less than 6 chain members from z. Mention may be made, as examples of radicals $R^1$, of:

$X'SO_2$— and $(X')_2PO$— radicals in which the group X' represents or the two groups X' represent, independently of one another:

a halogen, a $R^7CF_2$— radical in which $R^7$ is a halogen other than F or a carbonaceous radical preferably having at least 15 carbon atoms;

a perhalogenated radical $R_F$, preferably having a number of carbon atoms of less than or equal to 15, corresponding to the formula $R^8(CX''_2)p$- in which:

each of the X" groups represents, independently of one another, F, Cl or a perfluoroalkyl radical having from 1 to 5 carbon atoms (preferably 2 carbon atoms), at least one of the X" groups being F, preferably carried by the carbon connected to the sulfur, p being 1 or 2;

$R^8$ is an electron-withdrawing atom or radical having a σp of greater than 0 (preferably of greater than 0.1, more particularly of greater than 0.2), the possible functional groups of which are inert under the reaction conditions, for example an F or a perfluoroalkyl having at most 8 carbon atoms;

various radicals having a $\sigma_p$ of greater than 0.4, mentioned in particular in Advanced Organic Chemistry, $3^{rd}$ Ed., Gerry March, p. 244, such as, for example, COOR', COR', $SO_2R'$, $PO(R')_2$ or $PO(OR')_2$ in which R' is preferably an alkyl radical having from 1 to 15 carbon atoms or an aryl radical having from 6 to 20 carbon atoms.

In a preferred embodiment, $R^1$— represents an $X'SO_2$— or $(X')_2PO$— radical as defined above.

The substituent $R^2$ represents a carbonaceous and/or electron-withdrawing radical. When $R^2$ is an electron-withdrawing radical, it is advantageously chosen from the nitrile radical and the radicals defined above for $R^1$. When $R^2$ is a carbonaceous group, it is preferably chosen from radicals having from 1 to 20 carbon atoms.

When the compound (I) is liquid at the reaction temperature and when the ionic fluoride is soluble in said liquid compound, it is not essential to add a solvent to the reaction medium.

When the two reactants are in the solid form, the reaction is carried out in a liquid solvent. The solvent is aprotic when M is other than H.

When the solvation of the cation of the monovalent fluoride reactant is desired, use is preferably made of a solvent having a donor number from 10 to 30, preferably from 20 to 30. The donor number of a solvent represents the value $-\Delta H$, $\Delta H$ being the enthalpy (in kcal/mol) of the interaction between the solvent and antimony pentachloride in a dilute dichloromethane solution [cf. Christian Reinhardt, Solvent and Solvent Effects in Organic Chemistry, WCH, p. 19, 1988].

The solvents giving good results can in particular be amides, including amides with a specific nature, such as tetrasubstituted ureas and monosubstituted lactams. The amides are preferably substituted (disubstituted for ordinary amides). Mention may be made, for example, of pyrrolidone derivatives, such as N-methylpyrrolidone, N,N-dimethylformamide or N,N-dimethylacetamide. Another particularly advantageous category of solvents is composed of symmetrical or asymmetrical and open or closed ethers, including the various derivatives of glycol ethers, such as glymes, for example diglyme. Thus, the most appropriate solvents, because of their cost and their properties, are advantageously chosen from ethers (in particular cyclic ethers, such as THF, or polyfunctional ethers, such as glymes) or from amides not having acidic hydrogen, such as DMF or N,N'-dialkylalkyleneureas, among which may be mentioned DMEU (N,N'-Di-MethylEthyleneUrea) or DMPU (N,N'-DiMethyl- PropyleneUrea). Mention may also be made of N-methylpyrrolidone and cyclic ureas peralkylated on the nitrogens.

In addition, the solvent can be nitromethane.

It may be advantageous to add a phase transfer catalyst to the reaction medium, in order to improve the yield of the reaction. This addition is particularly of use when the reaction is carried out in a nonpolar or not very polar solvent. Mention may be made, as example of phase transfer catalyst, of quaternary ammonium salts, crown ethers, pyridinium salts or quaternary phosphonium salts. The addition of a phase transfer catalyst is targeted at overcoming a relatively low solubility of the alkaline ionic fluoride used. A highly soluble ionic fluoride which can be used as fluorination reagent in the process of the present invention can be used as phase transfer catalyst when it is combined with a fluoride reactant of low solubility. Mention may be made, by way of example, of onium fluorides and cesium fluoride.

The compounds (I) can be prepared by processes of the prior art. An imide salt can be prepared by the action on the corresponding imide of a salt, the acid form of which is volatile under the reaction conditions. For example, the action of an alkaline hydride on an imide in a protic medium makes it possible to obtain an anhydrous imide salt. It is also possible to react an alkylmetal compound, for example butyllithium, with an imide, in order to obtain the corresponding imide salt and an alkane, which is volatile if it is a lower alkane. In addition, it is possible to obtain an imide salt from the corresponding imide by exchange with a carboxylate with a sufficiently low molecular weight for the corresponding carboxylic acid to be volatile.

The present invention is illustrated by the following examples, to which, however, it is not limited.

EXAMPLE 1

3.556 g (137.1 mM) of LiF were introduced into 5 ml of nitromethane in a reactor and then the medium was stirred for 18 h in the presence of glass beads. A solution of 4.907 g (0.22926 mM) of bis(chlorosulfonyl)imide in 5 ml of nitromethane, corresponding to a LiF/imide molar ratio of approximately 6, was subsequently added dropwise with stirring. The reaction was allowed to continue overnight. A solid residue separated by settling and the supernatant solution was recovered for NMR analysis of the fluorine.

The analysis showed the presence of fluorine singlets at various chemical shifts and with different peak heights:

| Chemical shift | Peak height | Entity |
|---|---|---|
| 56.6 | 1 | $FSO_2NH_2$ |
| 50.8 | 78.4 | $(SO_2F)(SO_2Cl)NH$ |
| 54.5 | 12.7 | $SO_2F$ |
| 35.3 | 53.3 | $FSO_3^-$ |

After having continued the reaction for two weeks, different peak heights were obtained, the predominant compound being the desired lithium bis(fluorosulfonyl)imide.

EXAMPLE 2

4.111 g (19.205 mM) of bis(chlorosulfonyl)imide were dissolved in 5 ml of nitromethane. 6.549 g (155.97 mM) of finely divided NaF were added at 0° C. with continuous stirring. The NaF/imide molar ratio is of the order of 8. The reaction mixture was allowed to rise to ambient temperature and then was stirred in the presence of 3 glass beads for 60 h. After separation by settling, fluorine NMR analysis of the clear supernatant solution showed the presence of the desired product.

EXAMPLE 3

4.361 g (75.06 mM) of KF were suspended in 5 ml of nitromethane and then a solution of 3.176 g (14.84 mM) of bis(chlorosulfonyl)imide in 3 ml of nitromethane was introduced with continuous stirring. The KF/imide molar ratio is of the order of 5.

The reaction mixture heated up and the reactor was stirred with glass beads for 14 h. 3.49 g (60.034 mM) of fresh KF were then added and the mixture was stirred for a further 18 h. The solution became deep orange. After separating the solid particles by settling, the fluorine NMR analysis was carried out, which showed that the predominant product exhibits a chemical shift (singlet) of 51.6 ppm and corresponds to the conversion of 99% of the starting product. The predominant product obtained is potassium bis(fluorosulfonyl)imide.

The procedure of this example was employed in three additional tests, using, instead of bis(chlorosulfonyl)imide, $\phi SO_2NHSO_2Cl$, $CF_3SO_2NHSO_2Cl$ and $(\phi SO_2)_2CHSO_2Cl$ respectively, and the predominant formation of the following compounds was observed: $\phi SO_2NKSO_2F$ (from $\phi SO_2NHSO_2Cl$), $CF_3SO_2NKSO_2F$ (from $CF_3SO_2NHSO_2Cl$) and $(\phi SO_2)_2CKSO_2F$ from $(\phi SO_2)_2CHSO_2Cl$.

EXAMPLE 4

4.421 g (29.104 mM) of CsF were dispersed in 2 ml of nitromethane while stirring with glass beads. A solution of 2.243 g (10.480 mM) of bis(chlorosulfonyl)imide in 5 ml of nitromethane was added dropwise with stirring. The CsF/imide molar ratio is of the order of 3. After a reaction time of 72 h, followed by stirring for 6 h, fluorine NMR analysis of the supernatant liquid showed the following lines:

| Chemical shift | Peak height | Entity |
|---|---|---|
| 56.5 | 15.5 | $FSO_2NH_2$ |
| 52.1 | 48.3 | $(SO_2F)(SO_2Cl)N^-$ |
| 51.9 | 225.6 | $[N(SO_2F)_2]^-$ |

It thus emerges that 80% of the starting imide has been converted to bis(fluorosulfonyl)imide.

EXAMPLE 5

Bis(dichlorophosphoryl)imide was reacted with KF by a process analogous to that described in example 3. The conversion of the starting material with a yield of 90% and the predominant formation of potassium bis(difluorophosphoryl)imide was noted.

Bis(dichlorophosphoryl)imide can be prepared according to the process described by Riesel et al. [Riesel, Pfuetzner & Herrmann, Z. Chem., 23(9), 344–5, 1983].

What is claimed is:
1. A process for the fluorination of a compound (I) comprising reacting, optionally in a solvent, a fluorinating agent with said compound, wherein the fluorinating agent is an ionic fluoride of a monovalent cation and wherein the compound (I) corresponds to the following formula:

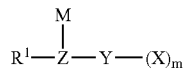

in which:
- M represents H, an alkali metal; a quaternary phosphonium group or a quaternary ammonium group;
- Z represents $CR^2$, N or P;
- Y represents $SO_2$ and m is 1, or Y is PO and m is 2;
- $R^1$ represents an electron-withdrawing group which has a Hammett $\sigma_P$ parameter of greater than 0.4;
- $R^2$ represents a carbonaceous and/or electron-withdrawing group;
- X represents a halogen other than fluorine.

2. The process as claimed in claim 1, which is carried out at atmospheric pressure.

3. The process as claimed in claim 1, which is carried out at a temperature between ambient and less than 180° C.

4. The process as claimed in claim 1, wherein the monovalent ionic fluoride is KF or CsF.

5. The process as claimed in claim 1, wherein the monovalent ionic fluoride is tetraalkylammonium, tetraalkylphosphonium or dialkylsulfonium fluoride.

6. The process as claimed in claim 5, wherein the alkyl groups of the tetraalkylammonium, tetraalkylphosphonium or dialkylsulfonium fluoride have from 1 to 12 carbon atoms.

7. The process as claimed in claim 1, wherein the ratio of the number of moles of fluoride to the number of halogen atoms to be exchanged of the compound (I) is greater than 1.

8. The process as claimed in claim 7, wherein the ratio of the number of moles of fluoride to the number of halogen atoms to be exchanged of the compound (I) is from 1.1 to 2.

9. The process as claimed in claim 7, wherein the ratio of the number of moles of fluoride to the number of halogen atoms to be exchanged of the compound (I) is greater than 2 when M is H.

10. The process as claimed in claim 1, wherein M represents H, an alkali metal, a quaternary ammonium $N(R^3R^4R^5R^6)$ or a quaternary phosphonium $P(R^3R^4R^5R^6)$, the various substitutents $R^3$, $R^4$, $R^5$, and $R^6$ being chosen, independently of one another, from alkyl radicals preferably having from 1 to 12 carbon atoms.

11. The process as claimed in claim 1, wherein the cation M is identical to the cation of the monovalent fluoride.

12. The process as claimed in claim 1, wherein $R^1$ is an electron-withdrawing group having a Hammett 0p parameter of greater than 0.7.

13. The process as claimed in claim 1, wherein $R^1$ and/or $R^2$ are an $X'SO_2$— or $(X')_2PO$— radical in which X' represents:
- a halogen,
- an $R^7CF_2$— radical in which $R^7$ is a halogen other than F or a carbonaceous radical;
- a perhalogenated radical $R_F$, corresponding to the formula $R^8(CX''_2)_p$— in which:
  - each of the X" groups represents, independently of one another, F, Cl or a perfluoroalkyl radical having from 1 to 5 carbon atoms, at least one of the X" groups being F, p being 1 or 2;
  - $R^8$ is an electron-withdrawing atom or radical having a $\sigma_P$ of greater than 0, the possible functional groups of which are inert under the reaction conditions.

14. The process as claimed in claim 13, wherein $R^7$ is a carbonaceous radical having at most 15 carbon atoms.

15. The process as claimed in claim 13, wherein at least one of the X" groups represents a perfluoroalkyl radical having from 1 to 5 carbon atoms.

16. The process as claimed in claim 13, wherein at least one of the X" groups is a F atom carried by the carbon connected to the sulfur or the phosphorus.

17. The process as claimed in claim 13, wherein $R^8$ is F or a perfluoroalkyl radical having at most 8 carbon atoms.

18. The process as claimed in claim 1, wherein $R^1$ represents a COOR', COR', $SO_2R'$, $PO(R')_2$ or $PR(OR')_2$ radical in which R' is an alkyl radical having from 1 to 15 carbon atoms or an aryl radical having from 6 to 20 carbon atoms.

19. The process as claimed in claim 1, wherein $R^2$ is a nitrile or a carbonaceous radical having from 1 to 20 carbon atoms.

20. The process as claimed in claim 1, which is carried out in an aprotic solvent.

21. The process as claimed in claim 1, wherein the solvent is nitromethane.

22. The process as claimed in claim 1, which is carried out in a solvent chosen from substituted or unsubstituted amides and symmetrical or asymmetrical and cyclic or noncyclic ethers.

23. The process as claimed in claim 1, wherein the reaction medium comprises a phase transfer catalyst.

* * * * *